United States Patent [19]

Gifford et al.

[11] Patent Number: 4,802,768
[45] Date of Patent: Feb. 7, 1989

[54] TWO LIGHT SOURCE REFERENCE SYSTEM FOR A FLUOROMETER

[75] Inventors: Charles R. Gifford, Foster City; Achille M. Bigliardi, Woodside, both of Calif.

[73] Assignee: Sclavo, Inc., Wayne, N.J.

[21] Appl. No.: 850,944

[22] Filed: Apr. 11, 1986

[51] Int. Cl.$^4$ .................. G01N 21/64; G01N 21/05
[52] U.S. Cl. ............................ 356/417; 250/458.1; 356/318; 356/246
[58] Field of Search ............... 356/301, 317, 318, 328, 356/319, 246, 435, 417; 250/458.1, 459.1, 461.1, 467.2, 458.1

[56] References Cited

U.S. PATENT DOCUMENTS

| | | | |
|---|---|---|---|
| 3,746,452 | 7/1973 | Teboul et al. | 356/435 X |
| 3,891,853 | 6/1975 | Kremen et al. | 250/458.1 |
| 3,918,812 | 11/1975 | Holm | 356/73 |
| 4,074,939 | 2/1978 | Rabl | 356/435 |
| 4,133,873 | 1/1979 | Noller | 424/8 |
| 4,320,970 | 3/1982 | Dowben et al. | 356/317 |
| 4,516,856 | 5/1985 | Popelka | 356/417 X |
| 4,622,468 | 11/1986 | Stefanski et al. | 250/458.1 |

FOREIGN PATENT DOCUMENTS 58-198733 11/1983 Japan ............................ 356/319

OTHER PUBLICATIONS

Lambert et al., *Canadian Journal of Microbiology*, 21:8:1232-1235, (1975) "Etude de la Stabilite et de la Degradation de la Fluorescence dans la Technique d'Immunofluorescence (FTA-ABS) a l'Aide de Lasers a Impulsions".

Kasatiya et al., *Applied Microbiology*, 27:5:838-843, (1974), "Use of Tunable Pulsed Dye Laser for Quantitative Fluorescence in Syphilis Serology (FTA-ABS Test)".

Bergquist et al., Scandinavian Journal of Immunology, 2:1:37-44, (1973), "The Pulsed Dye Laser as a Light Source for the Fluorescent Antibody Technique".

*Primary Examiner*—Vincent P. McGraw
*Attorney, Agent, or Firm*—Ron Fish

[57] ABSTRACT

A reference system utilizes pulsed arc light excitation which excitation pulses are directed onto a flow cell containing a fluorescent dye. Fluorescent light emitted from the dye is guided to a photomultiplier tube which converts it to electrical pulses. A portion of each excitation light pulse is guided by a light pipe onto a PIN diode light detector which converts these light signals to electrical pulses. A LED reference light source is pulsed to generate a plurality of reference light pulses one of which occurs between each excitation pulse. A portion of each of these pulses is guided to each of the two light detectors and two more series of electrical pulses are generated. A microprocessor then reads the four electrical pulses resulting from each pair of light pulses and performs a computation on the resulting numbers which indicates the relative concentration of the target concentration being assayed. An optical system masks the excitation light pulses and the emitted light pulses to minimize the amount of scattered excitation light that gets into the emitted light optical channel and spatially integrates the images of the arc yielding the excitation light to control the stability of the image projected onto the photomultiplier tube. The light pipe and an output lens spatially integrates the image of the excitation light mask and focuses this light on the PIN diode so that the dancing image of the arc does not modulate with the variations of the PIN diode cathode and destabilize its output signal.

18 Claims, 7 Drawing Sheets

TWO LIGHT SOURCE REFERENCE SYSTEM FOR A FLUOROMETER

BACKGROUND OF THE INVENTION

The invention pertains to the field of fluorometers in general, and to reference systems for such fluorometers to promote stability and accuracy in particular.

In biological research it is often useful to assay samples containing trace amounts of various chemicals, hormones or enzymes that exist in the human body. In the past, such assays have been done with radioisotopes in which are called radioimmunoassays and such assays have also been done with fluorometers. Radioimmunoassays utilize radioactive isotopes to "tag" the target molecules or proteins of interest, i.e., the radioactive isotopes are attached to the molecules or proteins of interest in known tagging processes. The quantity of the molecules or proteins of interest (hereafter the targets) in the sample can then be deduced by counting the number of radioactive events which originate in the sample in a given period of time. The difficulty with this type of assay is that the radioisotopes have shelf lives which must be monitored since they lose their radioactivity over time. This reduces the effectiveness of any assay done using a weakened isotope. Further, disposing of such radioactive samples and unused radioisotopes without posing a danger to society is difficult and expensive.

Assays using fluorometers involve use of fluorescent dyes called fluorophores which fluoresce or emit light when excited with excitation light in the excitation band of the particular fluorophore being used. These fluorophores are used to tag the targets in a similar manner to use of radioisotopes to tag the target. Hereafter when the term "sample" is used, it is to be understood as referring to the sample molecules of interest as tagged with one of the fluorophores. Alternatively, sometimes the term dye will be used as a synonym for the tagged sample molecules.

Such fluorometer assays are much more desirable than radioimmunoassays since they do not use radioisotopes. However, a problem arises with these fluorometer assays where extremely small amounts of the target is present in the sample. The problem has been that the fluorometer system itself could not be made stable enough to prevent noise from degrading the answer. That is, it has been difficult or impossible to eliminate the effect on the answer calculated by the system of changes in the system other than changes in the amount of the sample concentration. Such changes, if not neutralized or eliminated, can destroy the accuracy of the answer calculated by the system.

Typically, the sample concentration of interest in fluorometer-type assays involve very low concentrations of the molecules of biological entities of interest. For example, sample concentrations of from $10^{-8}$ to $10^{-13}$ are not uncommon. To assay such low sample concentrations using fluorophores requires that a very intense light source emitting radiation having a wavelength in the excitation band of the fluorophore be used. Further, all emitted light from the fluorophore must be efficiently collected and quantized, and the effect on the system of changes in the sensitivity of the emitted light detectors over time or changing temperatures must be eliminated to get accurate results.

The desired end result is a number called the relative fluorescence intensity. This number is an indication of the sample concentration, and it is expressed in terms of a ratio. That ratio is calculated by dividing the intensity of the emitted fluorescent light by the intensity of the light from the light source used to excite the fluorophore. To do this requires that some light detector be used to detect the intensity of the emitted fluorescent light, and the same or a different light detector be used to detect the intensity of the excitation light. The two signals representing these two intensities may then be divided to arrive at the relative fluorescence intensity.

Two systems or general approaches have evolved in the prior art for generating the signals representative of the intensity of the emitted fluorescent light and the intensity of the excitation light. The first such system is illustrated in FIG. 1. This type system used a continuous light source and a single detector. Two light paths to the single detector are used. The first is the sample path which includes excitation light traveling from the light source to the sample along the excitation path through the first beam splitter and a light chopper. The emitted fluorescent light from the sample passed through the second beam splitter to the detector. The second light path is the reference path to the detector. Light on this path travels from the light source to a first beam splitter where part of it is directed downward along the reference path where it is deflected around the sample container by two mirrors and through the light chopper. This light then travels to the second beam splitter where part of it is deflected onto the face of the detector. The chopper serves to chop the continuous light beam from the light source traveling along the excitation light path and the reference light path into two light pulse trains which are interleaved in time. This interleaving is such that a pulse will illuminate the sample and cause a burst of emitted fluorescent light. This burst will be detected and a signal indicating its intensity will be generated and switched onto channel 1. Following this chain of events, a pulse of light that has traveled along the reference light path will arrive at the detector, and will be converted to an electrical signal which will be switched into channel 2. These two signals on channels 1 and 2 can be divided to derive the relative fluorescence index (hereafter sometimes referred to as the RFI).

Several difficulties exist with the system of FIG. 1. First, it is difficult to get very high intensity light in the proper wavelength out of the light source without generating a large amount of heat which shortens the life of the lamp, must be dissipated, and which may heat up the sample, thereby changing its fluorescent light emitting characteristics. Heating the sample can result in an apparent change in sample concentration even though no actual change occurred. Further, a great deal of excitation light energy is lost by being diverted down through the reference channel. Specifically, every other pulse is completely lost as the chopper blocks the excitation path and only allows light to pass along the reference path. This translates into a lower excitation efficiency in terms of the total amount of time the light is on compared to the total time the sample is being excited.

To circumvent such difficulties, the system of FIG. 2 evolved. The system of FIG. 2 used a single pulsed light source, but used two light detectors instead of one. The first light detector detected the intensity of the emitted fluorescent light from the sample. The second light detector detected the light intensity of each excitation light pulse. A beam splitter was used to divert some light energy from each excitation light pulse into the second light detector.

The system of FIG. 2 represents an improvement over that of FIG. 1. First, a pulsed light source means that higher intensity pulses can be generated by elevating the black body temperature of the light source to high enough levels to generate light of the optimal wavelength for excitation. Because this is done in a pulsed fashion, a large amount of heat is not generated, thereby minimizing sample heating, easing the heat dissipation problem, and extending the life of the light source. Since every pulse is used for excitation, the excitation efficiency is improved.

However, while the system of FIG. 2 represents an improvement over that of FIG. 1, there were new difficulties created by the system of FIG. 2. Principally, these difficulties involved the potential creation of errors in the calculated RFI caused by the changes in the system other than changes in the sample concentration. For example, it is important in the system of FIG. 2 for the characteristics of the two detectors to be matched in their drift characteristics. If the temperature of the ambient environment changes or the aging process causes the responses of the two detectors to change relative to each other in response to a single pulse, then that change will show up as an error in the RFI and an apparent change in the sample concentration when, in fact, there was no such change.

Thus, a need has arisen for a fluorometer system which solves the aforementioned problems such that stable RFIs can be computed with minimal error for sample concentrations in the range of from $10^{-8}$ to $10^{-13}$ molar concentration of the fluorophore.

SUMMARY OF THE INVENTION

The invention is a reference system which improves the stability and accuracy of a reference system for the fluorometer. The reference system neutralizes the effects of many changes in the fluorometer system other than changes in concentration of the target in the sample.

The reference system uses a first pulsed excitation light source and a second pulsed reference light source and two detectors. Typically, the pulsed excitation light source is a high intensity arc light where the arc wanders randomly in the space between the electrodes. There is an optical path for guiding the excitation light pulses to a flow cell containing the sample tagged with a suitable fluorophore such as fluorescein. The excitation light pulses have optical spectra in the excitation band of the particular fluorophore selected. In response to each excitation light pulse, the fluorophore becomes excited, i.e., some electrons are kicked into higher energy orbital states by absorption of energy from the incoming photons. Many of these excited electrons decay to lower energy orbits giving up photons which are seen as fluorescent light emitted from the sample. A second optical path guides this fluorescent light to a first of the two light detectors, typically a photomultiplier tube (sometimes hereafter referred to as the "PMT") which detects the light and outputs a signal indicative of the intensity of the fluorescent light. The amplitude of this signal is stored as a variable A which is indicative of the amount of the excited fluorophore in the sample which is indicative of the concentration of the sample.

A portion of each excitation light pulse is also guided to a second light detector by a light pipe. The second light detector outputs a signal which has an amplitude which is stored as a variable B. This amplitude signal B is indicative of the intensity of the excitation light pulse. A second light source, typically a light emitting diode, is pulsed alternately with the excitation light source to generate reference light pulses which are interleaved in time with the excitation light pulses. A portion of each of these reference light pulses is propagated to each of the first and second light detectors. In response to each of these reference light pulses, each of these first and second light detectors outputs a signal which is indicative of the intensity of each reference light pulse. The output of the first detector in response to each reference pulse is stored as a variable D, and the output of the second detector in response to each reference pulse is stored as a variable C. The system also measures the output of each of the detectors in the absence of any light pulses and stores the output of the first detector as a variable Z1 and stores the output of the second detector as a variable Z2. The system then calculates the RFI of the sample by calculating $(A-Z1)/(B-Z2)$ times $[(C-Z2)/(D-Z1)]$. Most variations in signal levels due to fluctuations in the two light sources in terms of intensity from pulse to pulse or wavelength shifts or due to variations in the responses of the first and second detectors or due to variations in the other electronic and optical components of the system are eliminated through use of this ratio.

The advantages of the reference system of the invention include all the advantages for the pulsed light system of FIG. 2 discussed earlier herein. Principally, the advantage of a pulsed light system is that very high intensity pulses can be generated using a high black body temperature. This generates excitation energy having wavelengths in the blue range of the excitation band without generating excessive heat and shortening the life of the lamp. Among the principal advantages of using the two detectors is that the effect of variations in the response characteristics of the two detectors or variation in the intensity of the excitation light pulses from pulse to pulse for any reason are canceled out. This is because of the particular ratio used to calculate the RFI. As will be apparent from the discussion below, any variations in the response characteristics such as the sensitivity of the PMT light detectors are canceled out because there is a PMT response factor in both the numerator and the denominator of the RFI fraction. The same is true for any variations in the response characteristics such as the sensitivity of the PIN diode light detector. Any variation in intensity from pulse to pulse in the light pulses from the excitation light source is canceled out because there is a term in the RFI fraction proportional to the intensity of the excitation light pulse in both the numerator and the denominator. The same is true for variations from pulse to pulse in the intensity of the light pulses from the LED reference light source.

The optical system of the invention provides certain improvements to the operation of the reference system to further improve the stability and signal to noise ratio of the system. Typically, a pulsed, broadband, incoherent, high intensity arc light is used to provide the excitation light pulses although a laser could also be used. Such broadband pulsed light sources are more effective than continuous light sources because they can give more intense light in the excitation band without excessive heating of the sample. Such heating can cause changes in the system which are undesirable. Higher intensity of light in the excitation band excites more of the fluorophore molecules thereby improving the signal to noise ratio by increasing the intensity of the fluorescent light emitted by the sample.

Further improvement in the stability of the system can be made by using a carefully sized aperture in a mask in the optical path between the excitation light source and the sample-containing flow cell. The reason for use of this mask and aperture is to limit the geometric bounds of the arc image to a known area to minimize scatter of excitation light into the fluorescent light optical channel. Arc flash lamps use two electrodes between which an arc is formed. This arc wanders randomly between these electrodes, but by use of a mask and aperture, the wandering image of the arc projected upon the sample through the excitation light input window in the flow cell can be framed or spatially limited, i.e., limited to a specific, known area which is controlled in such a way as to minimize scatter. Scatter is minimized because little energy is allowed to fall on the structure of the flow cell outside the boundaries of the input window. That is, no rays of the image of the mask aperture fall upon areas of the flow cell outside the input window. The image of the mask aperture is projected into and focused approximately at the center of the flow cell. This masking decreases the amount of excitation light scattered from corners of the flow cell. This scattered excitation light may find its way into the optical path traveled by the emitted light from the sample to the first detector. Since there is typically some slight overlap in the passbands of the excitation light and emitted light filters, minimization of scattering or coupling of the excitation light into the fluorescent light path improves the signal to noise ratio of the system.

Such coupling between the excitation light path and the fluorescent emitted light path is called crosstalk. It is very desirable to eliminate crosstalk since it can easily overwhelm the emitted light from the sample. This emitted light is very weak, because the concentration of the targets in the sample fluid is small in assays where the invention is most useful.

The photocathodes of photomultiplier tubes often are not uniform over all areas of the surface in terms of signal output generated for light falling on any given spot for a given input light intensity. As a result, if a structured image such as an image of an arc is allowed to wander randomly across the face of the photocathode, variations in the amplitude of the output signal may result. The invention eliminates the possibility of such variations through the use of spatial integration to destroy the arc image. Specifically, in the optical path for the excitation light, the arc image is masked to limit its geometric bounds, and this masked image is projected into the flow cell input window where it excites the fluorophore molecules. The fluorophore molecules then emit photons randomly in all directions which, statistically, forms a spherical pattern. The resultant emitted fluorescent light is spatially integrated, and appears to the PMT as a uniformly glowing image of the output window of the flow cell. This uniform image prevents the variations in photocathode sensitivity from affecting the amplitude of the output signal as they otherwise would if a wandering arc image was projected onto the photocathode.

In the optical path for the reference light pulses, a spatial integration is also used for the same purpose. In this reference light path, multiple internal reflections in the light pipe cause the spatial integration. Masking is also used in the reference path for the same purpose as masking was used in the excitation path.

By virtue of the masking and spatial integration of the arc image in both the excitation and reference optical paths, both paths maintain a true proportionaltiy. This results in a compensated, stable signal free from instabilities or variations caused by arc image wandering or pulse amplitude variations.

Further improvement in the operation of the system is achieved by using a mask with a carefully sized aperture in the optical path between the flow cell output window and the PMT photocathode. This mask and aperture are located in the plane of the focused image of the output window of the flow cell. The aperture is sized to allow the emitted light from the flow cell output window to just slightly underfill the photocathode of the PMT. This underfill is preferred, because overfill results in lost light and a lower signal-to-noise ratio. However, the underfill is not so much as to result in a small spot on the surface of the photocathode which could result in undesirable saturation at higher sample concentrations. The optimal aperture size will result in filling the photocathode as closely as possible to 100% utilization.

Another advantage of using this mask between the flow cell output window and the PMT photocathode is that it cuts down the amount of scattered excitation light which reaches the PMT. Excitation light which inadvertently strikes the walls or corners of the flow cell may be scattered into the optical path from the flow cell to the PMT. If this scattered excitation light is detected by the PMT, it will cause an error and could saturate the PMT because of the intensity of the excitation light. The mask in front of the PMT blocks this scattered light from reaching the PMT.

An optical passband filter is used in the optical path between the excitation light source and the flow cell. This filter transmits excitation light through to the flow cell, but substantially blocks transmission of light having wavelengths outside a desired range of excitation light wavelengths to the flow cell. Another optical passband filter is used in the fluorescent light optical path between the flow cell and the photomultiplier tube. This filter is selected to have a passband that transmits light in the range of wavelengths emitted by the dye molecules and blocks any wavelengths which lie in the passband of the excitation filter.

Changes in the wavelength of the light pulses emitted from the reference LED are minimized by stabilizing its temperature. This is done by constantly driving the LED with a pulse train of electrical pulses having a frequency of 1000 hertz although use of this particular frequency is not critical. This causes the LED to heat up to an operating temperature and stay at that temperature since the LED is never shut off. Any driving frequency which results in stabilization of the LED temperature will suffice.

In short, a principal advantage of the invention is that signal variations due to changes in the pulsed light sources, and due to changes in the first and second light detectors can be substantially eliminated by the improvements mentioned above. A very stable reference system is thus provided which can accurately detect and quantify trace amounts of a protein or molecule of interest.

DETAILED DESCRIPTION OF THE PREFERRED EMBODIMENT

Figure 3:
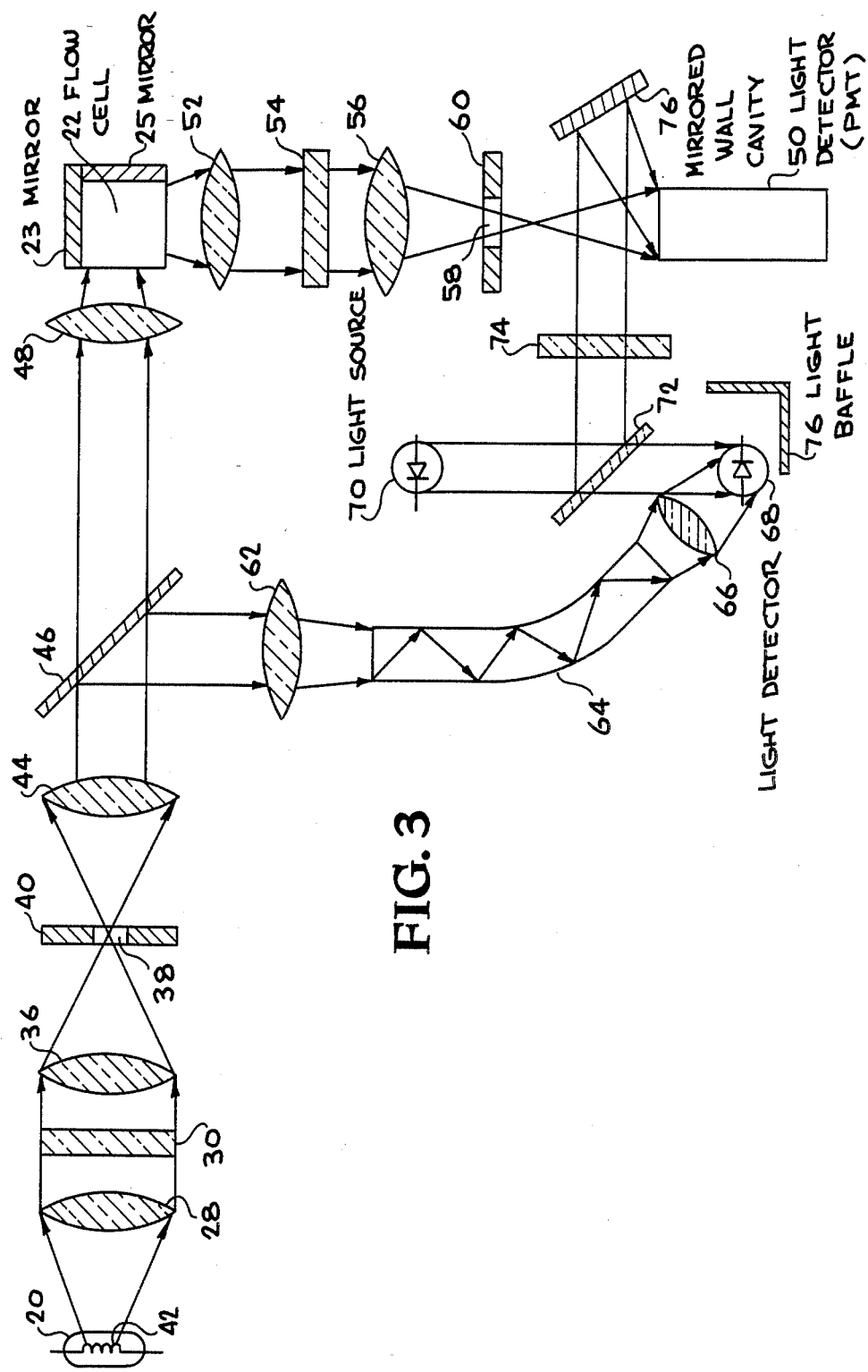
FIG. 3 is a block diagram of the fluorometer system of the invention.

Referring to FIG. 3 there is shown a schematic diagram of the invention intended to illustrate the principal elements of the reference and optical systems of the invention. The precise details of the optical system configuration will be given below in a separate section on the optical system.

Figure 1:
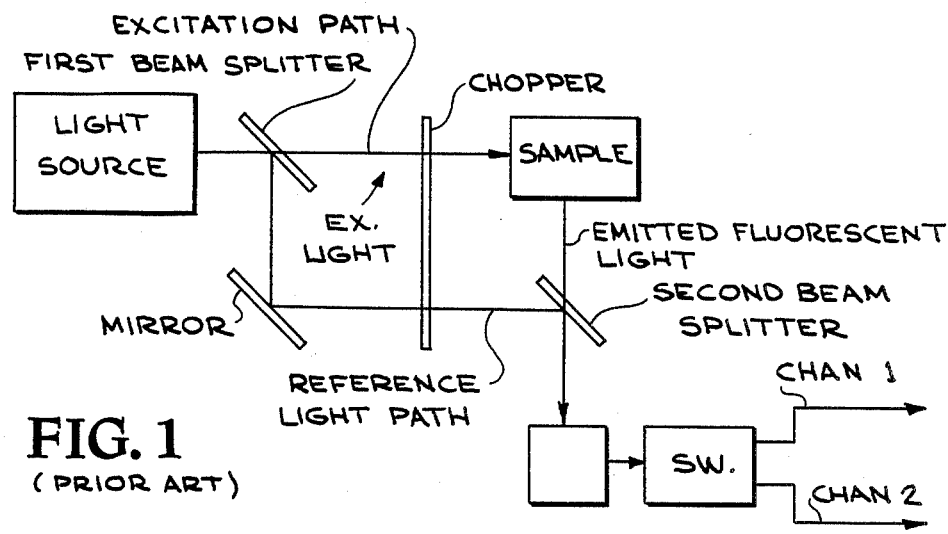
FIG. 1 is a block drawing of one type of known reference system.
Figure 2:
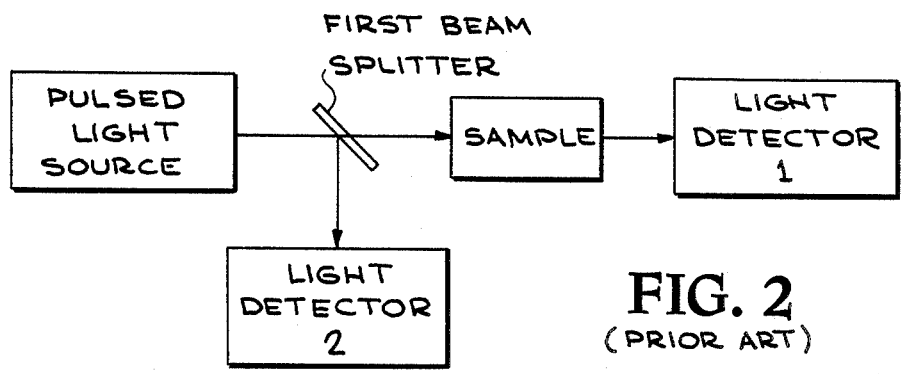
FIG. 2 is a block diagram of an improved type of known reference system.
Figure 4:
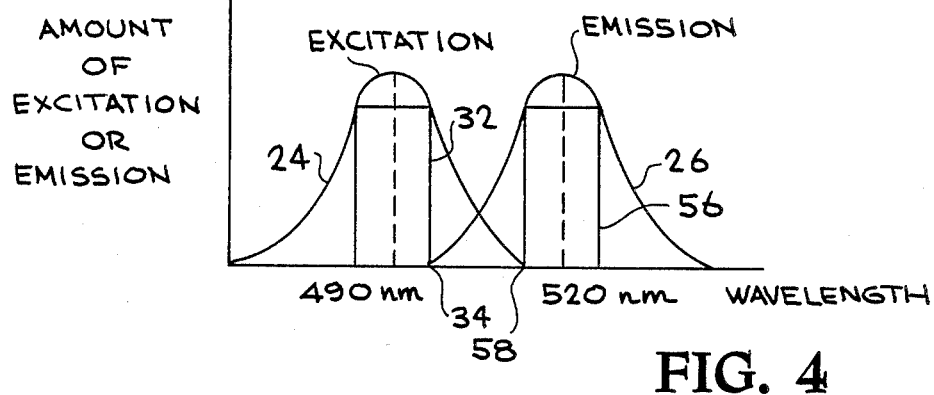
FIG. 4 is a plot of the excitation and emission bands of the fluorophore and the passbands of the optical filters.

For purposes of properly framing the discussion of the reference system of the invention, a brief discussion of the general operation of the fluorometer will be included prior to detailing the structure and operation of the reference system. A light source 20 provides excitation light for the particular fluorophore used to tag the sample molecules mixed in the fluid in a flow cell 22. Each fluorophore has a particular excitation band of wavelengths for incoming light which will excite fluorescence in the fluorophore. Each fluorophore also has an emission band of wavelengths for the fluorescent light emitted in response to excitation by incoming light in the excitation band. FIG. 4 illustrates the excitation and emission bands for a commonly used fluorophore, fluorescein. This dye has an excitation band 24 which has a peak at approximately 490 nanometers and has an emission band 26 which has a peak at 520 nanometers. Note that the excitation and emission bands overlap somewhat.

The light souce 20 can be any light source which provides a sufficiently intense light output in the excitation band of the particular dye being used. Higher intensities of light output in the excitation band are desirable since higher intensity light means more photons of the proper frequency are emitted. Greater numbers of photons in the excitation band means greater numbers of dye molecules on targets will be excited and will emit light in the emission band. This increases the signal which is the object of the quantification efforts (the emitted light from the dye in response to excitation) thereby increasing the signal to noise ratio and improving the sensitivity of the detection system. The light source 20 can be a laser emitting monochromatic, coherent light somewhere in the excitation band, preferably at or near its peak. In the preferred embodiment, the light source 20 is a high intensity, broad band, high pressure Xenon arc lamp which is pulsed by a conventional computer controlled driver (not shown). The pulsing of the light 20 allows a very high intensity pulse of 1–2 microseconds in duration. The pulse rate of the light 20 is in the range from 10–1000 hertz in the preferred embodiment. This slow pulse rate and short pulse width allows the light 20 to be driven to very high black body temperature without excessive heat generation and excessive infrared components in the emission spectrum of the light. The high black body temperature is desirable because it increases the intensity of the blue light component in the output spectrum, i.e., maximizes light emission around the excitation band peak. The inherent efficiency of a pulsed light source as compared to a continuous light source allows for the reduction of heat generation and prevents convection and radiation heating of the sample. Heating of the sample is undesirable since the intensity of the fluorescent light emitted from the sample for the same target concentration changes for increasing sample temperature even though the concentration of the targets remains unchanged. Thus, heating of the sample by the light source 20 would cause an undesirable drift in the system or change in the apparent concentration of the target which would be erroneous.

Because the light emitted from the light 20 emerges at all angles, and because it is desirable to capture the maximum amount of emitted light and direct it onto the flow cell to improve the signal to noise ratio, a collimating lens 28 is used to capture emitted light in its numerical aperture and project it in a column.

This column of light is projected through a filter 30 which is a "complete blocking passband filter" constructed to pass as much light as possible in a specific passband but to substantially block passage of all radiation wavelengths outside this passband including infrared or ultraviolet radiation. Referring to FIG. 4, the box 32 symbolically illustrates the shape of the passband. The actual edges of the passband are not vertical but are, in fact, somewhat sloped. The steepest slope cutoff for the passband edges which can be made with conventional filter techniques is desirable since the peak of the passband of the excitation spectrum filter must otherwise be shifted off the peak of the excitation spectrum enough such that the sloped edge nearest the emission filter spectrum reaches a very low transmission level at a wavelength shorter than the shortest wavelength in the emission filter spectrum, i.e., the wavelength at point 34. This is necessary to avoid crosstalk in the form of scattered excitation light being detected as emitted light. The specifications which completely define the filter 30 are that its half power points are at 488.3 nanometers (+0 nm−1.5 nm tolerance) and 478.3 nm (+ or −2 nm tolerance). The transmission factor for the filter 30 at 496 nm is $10^{-6}$ maximum. Any filter which matches these specifications will be adequate for purposes of practicing the invention. There are commercial filter manufacturers which are capable of manufacturing filters having these specifications using known techniques, so the details of their manufacture will not be given here.

After passage through the filter 30, the excitation light pulses are focused by a lens 36 on a aperture 38 in a mask 40. The purpose of this aperture is to block transmission of excitation light outside of the known boundaries of the aperture 38. The reason for this will be discussed more fully below in connection with discussion of the optical system. The image of the arc 42 in the light 20 is in the plane of the aperture 38.

Next, a lens 44 recaptures the diverging light from the aperture 38 and collimates it for transmission toward the flow cell 22. The collimated beam of light passes through a beam splitter 46 which passes most of the beam, but the beam splitter diverts approximately 9% of the excitation light into a reference optical path to be described below.

A lens 48 focuses the image of the aperture 38 through a transparent input window in the flow cell into the sample contained within the flow cell 22. The opposite side of the flow cell from the input window is a mirror 25 which reflects any excitation light or emitted light back into the sample. The sample molecules then fluoresce, thereby emitting light in all directions. A transparent output window allows photons to escape into an optical path designed to guide the fluorescent emitted light to the surface of a light detector 50. A mirror 23 on the surface of the flow cell opposite the light detector 50 reflects photons traveling away from the light detector 50 back toward and through the output window.

These emitted photons or light rays diverge at various angles after leaving the flow cell output window. A lens 52 captures a portion of the emitted photons and collimates them into a beam of parallel rays.

Another passband filter 54 is interposed between the flow cell 22 and the light detector 50 to block transmission of most radiation outside its passband. The passband of the filter 54 is symbolized by the box 56 in FIG. 4. The object for this filter is to pass light within the emission spectrum of the excited dye and to block transmission of substantially all other radiation to eliminate crosstalk and to prevent scattered excitation light from being detected falsely as emitted fluorescent light. The edges of the passband 56 are not really vertical, but are slightly sloped as is the case for the filter 30. Ideally, the filter would have a vertical rolloff, but in reality, the rolloff is sloped. The filter is manufactured with as steep a rolloff as possible, with the peak of the passband nearly centered on the emission spectrum. The filter must substantially block all light energy having a wavelength shorter than the wavelength at the point 58. The complete specifications for the filter 54 are that it is a "bandpass filter only" with half power points at 513 nm (tolerance $+1.5$ or $-0$ nm) and 523 nm (tolerance $+$ or $-2$ nm). Its transmission factor at 507.5 nm is $10^{-6}$ maximum. Both the filters 30 and 54 can be built with conventional filter manufacturing techniques.

After passing through the filter 54, the collimated, filtered fluorescent light passes through a focusing lens 56. As the light of the excitation pulses falls on the sample in the flow cell 22, and photons are emitted in random directions, and the image of the moving arc inside the aperture 38 is destroyed, i.e., spatially integrated into a glowing amorphous area of light. In order to prevent stray excitation light scattered from the flow cell walls from reaching the light detector, a lens 56 is used to focus the image of the flow cell 22 into an aperture 58 of a mask 60. This aperture 58 masks the walls of the flow cell image, and passes only those light rays emanating from within the flow cell.

The intensity of the emitted light is then detected by the light detector 50 and converted into an electrical signal. Typically, the light detector 50 is a photomultiplier tube, but other very sensitive light detectors could also be used.

THE REFERENCE SYSTEM

The beam splitter 46 deflects a small portion of the excitation light pulse energy into a lens 62. The percentage of light energy so deflected is not critical, but it should be at least high enough to be readily detected and converted into a signal, and should not be so high as to drain substantial excitation light energy away from the task of exciting the dye molecules. The lens 62 focuses the image of the aperture 38 onto the input end of the light pipe 64. Typically, the light pipe 64 is a clear plastic rod with a cladding having an index of refraction which is sufficiently different from the core to cause internal reflections of light rays impinging on the cladding at less than the critical angle. The lens 62 should be located and configured so as to focus the arc image within the aperture of the light pipe 64. Some losses from the light pipe will not be fatal since the 9% of diverted excitation light energy is more than enough for purposes of the reference system's operation.

The light pipe 64 guides the injected light by internal reflections to an output end where the guided light emerges at many different angles. The light pipe 64 spatially integrates in that the image of the arc and mask aperture is destroyed by the thousands or millions of internal reflections of the rays making up the image. The light emerging from the output end represents a glowing, homogeneous disk of light pulsing in time with the excitation pulses. The image of the wandering arc is completely destroyed.

The emerging light from the output end of the light pipe 64 is captured by a lens 66 and projected upon a second light detector 68. This light detector 68 is typically a PIN diode which converts incoming light pulses into electrical pulses having amplitudes which are related by the transfer function of the diode to the intensity of the incoming pulses.

A second light source 70, typically a green light emitting LED, is driven by a computer-controlled pulse driving system (not shown) to emit reference pulses which are interleaved in time with the excitation pulses. That is, in between every excitation pulse, the LED 70 will be driven to the "on" condition to emit a reference light pulse.

Each reference pulse is directed by the lens of the LED itself toward the light detector 68 through a beam splitter 72. The beam splitter 72 allows some of the reference pulse light energy to pass straight through and diverts some of each reference light pulse generally toward a mirrored wall cavity 76. Each of these reference light pulse portions which pass straight through the beam splitter 72 is converted into an electrical pulse having an amplitude which is related to the intensity of the portion of the reference light pulse which struck the light detector 68.

The portion of each reference light pulse which is diverted by the beam splitter 72 toward the mirrored wall cavity 76 and the light detector 50 passes through a filter 74. The filter 74 attenuates the relatively intense green light from the LED to a level which will not saturate the photomultiplier tube 50. The filter 74 also acts as a passband filter to pass the green light from the LED while blocking any scattered blue excitation light that happens to get into the optical path between the beam splitter 72 and the photomultiplier tube 50. Although only shown schematically, there is a light baffle 76 in the form of a dark wall arranged so that very little blue excitation light gets scattered toward the photomultiplier tube 50 from the end of the light pipe 64 the lens 66 or from the PIN diode 76.

The filter 74 can be an inexpensive filter since the difference in wavelength between the green reference light pulses and the blue excitation pulses can be controlled to be far enough apart to allow a simple filter to be used.

The reference light pulses that pass through the filter 74 are directed into a cavity 76 which has polished aluminum walls. The incoming light pulses are reflected between the walls of the cavity so as to again spatially integrate the image of the LED 70 thereby destroying the image. However, this spatial integration is not necessary since the image of the LED is stable. The references pulses are reflected in the cavity 76 so as to be redirected onto the face of the photomultiplier tube 50 where each reference pulse is turned into an electrical signal having a magnitude which is proportional to the intensity of the reference light pulse.

Figure 5:
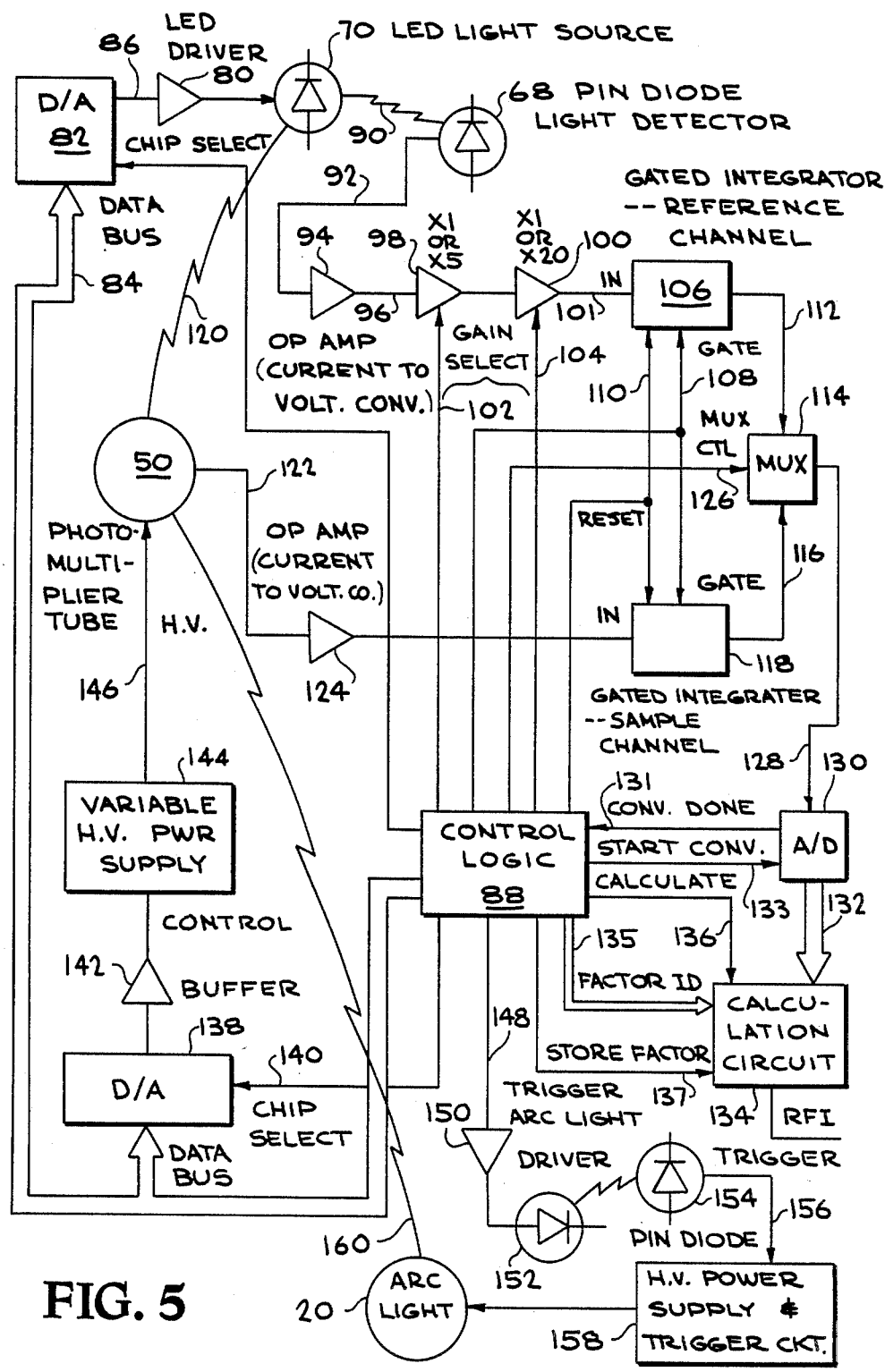
FIG. 5 is a block diagram of the electronic portion of the reference system.

Referring to FIG. 5 there is shown a block diagram of the electronic circuitry which is part of the reference system. The LED reference light source 70 is driven by a LED driver 80 which is coupled to the output of a D/A converter 82. The D/A converter 82 converts the data on the data bus 84 into an analog voltage on the line 86 which is converted to a proportional drive current which is driven through the LED 70. The data and the timing of the data on the data bus 84 is controlled by control logic 88 which serves to generate the various data and control signals that control the operation of the reference system. The functions and timing relationships of these control and data signals will be described more fully below. By controlling the data on the data bus 84 and the time at which it appears, the control logic 88 is able to cause the LED 70 to generate the reference light pulses at varying intensities. The reason the ability to vary the intensity of the reference light pulses is desirable is that the gain of the system is adjustable, and when the gain is turned down, it is desirable to be able to turn the intensity of the reference light pulses up by a similar factor.

The reference light pulses 90 are optically coupled to the PIN diode light detector 68. This diode converts the incoming light to a current in the line 92 which is proportional to the intensity of the reference light pulses. An operational amplifier 94 coupled as a current to voltage converter converts the current signal to a voltage signal on the line 96. This signal is processed by two operational amplifiers 98 and 100 which have variable gains controlled by the signals on the lines 102 and 104 respectively. The amplifier 98 amplifies the signal on the line 96 by either a factor of either 1 or 5 depending upon whether the line 102 carries a logic 1 or a logic 0. The amplifier 100 amplifies the signal at the output of the amplifier 98 by a factor of either 1 or 20 depending upon whether the line 102 carries a logic 1 or a logic 0. By suitably controlling the signals on the lines 102 and 104, gains of 1, 5, 20, or 100 can be selected. The output signal from the amplifier 100 is coupled via a line 101 to the input of a gated integrator 106. This gated integrator sums the signal on the line 101 beginning at the time a GATE signal on a line 108 is asserted. The gated integrator is somewhat similar to a sample and hold circuit in that when the GATE signal is not asserted the result of the integration is held. The result is held until the gated integrator 106 receives a RESET signal on a line 110, at which time, the output on the line 112 goes to zero and the gated integrator is ready to integrate the next pulse.

The output of the gated integrator is coupled to a port on a multiplexer 114. The other port of this multiplexer 114 is coupled to the output line 116 of another gated integrator 118 which serves to integrate the signal from the photomultiplier tube light detector 50. The reference light pulses 120 which fall upon the photomultiplier tube 50 are converted to current pulses which are output on a line 122. These current pulses are converted to voltage pulses by an operational amplifier 124 and applied to the input of the gated integrator 118. This gated integrator has its reset input coupled to the line 110 and its gate input coupled to the line 108 and functions the same way the gated integrator 106 functions. The control logic 88 controls the lines 110 and 108 with the signals GATE and RESET in a manner which will be described below when the operation of the system to accomplish its intended purpose is described.

The multiplexer 114 selects the signal on one of its two input ports 112 and 116 according to the state of the MUX CONTROL signal on a control line 126 from the control logic 88. The selected signal is coupled to an output line 128 which is coupled to the input of an A/D converter 130. The analog signal on the line 128 is converted to a digital value which is output on a factor bus 132 which is coupled to a calculation circuit 134. The calculation circuit 134 performs the calculation to be described below after storing all the factors needed in memory as they are received on the factor bus 132. In the preferred embodiment, the control logic 88 and the calculation circuit 134 are a suitably programmed microprocessor (Z80) for which the assembly code is included herewith as Appendix A. However any other analog or digital embodiment which generates the signals described above in the sequence to be described below and which performs the calculation to be described below will suffice for purposes of practicing the invention. After receiving and storing all the factors, the calculation circuit can automatically perform the calculation or perform it upon receipt of a signal on a line 136. In the preferred embodiment, the signal on the line 136 also tells the calculation circuit the gain at which the measurements were taken. The meaning and purpose of the other control signals coupling the control logic 88 to the A/D converter 130 and the calculation circuit 134 will be explained below in conjunction with a discussion of the timing of the control signals to implement the calculation performed during every read cycle.

The control logic 88 also is coupled by the data bus 84 to a digital to analog converter 138. The data on the data bus 138 is converted to an analog number when the chip select line 140 coupling the control logic to the digital to analog converter 138 is active. The chip select line 140 could be the output of an address decoder or could symbolize an address bus with the address decoder in the D/A converter 138. The analog output of the D/A converter 138 is buffered by a buffer 142 and applied as a CONTROL signal to the control input of a variable voltage high voltage power supply 144 which outputs a high voltage for biasing the photomultiplier tube 50 on a line 146. By varying the data on the data bus 84 with the D/A converter 138 selected, the high voltage to the photomultiplier tube can be controlled to control the sensitivity of the system.

The control logic 88 is also coupled to the arc light to control its flash rate. A TRIGGER ARC LIGHT signal on a line 148 is asserted by the control logic 88 when the arc light 20 is to be triggered. This signal is coupled to the input of a driver amplifier 150 which has its output coupled to drive a light emitting diode. The light emitted by the LED 152 during the assertion of the TRIGGER ARC LIGHT signal falls upon a PIN diode 154 which detects the light pulse and generates a TRIGGER signal on a line 156 which is coupled to a high voltage power supply with a trigger input. When the TRIGGER signal occurs, the high voltage power supply 158 sends a high voltage, high current pulse through the arc light 20 to create an arc and generate an excitation light pulse 160 which is coupled to the photomultiplier tube 50 through generation of emitted fluorescent light.

Figure 6:
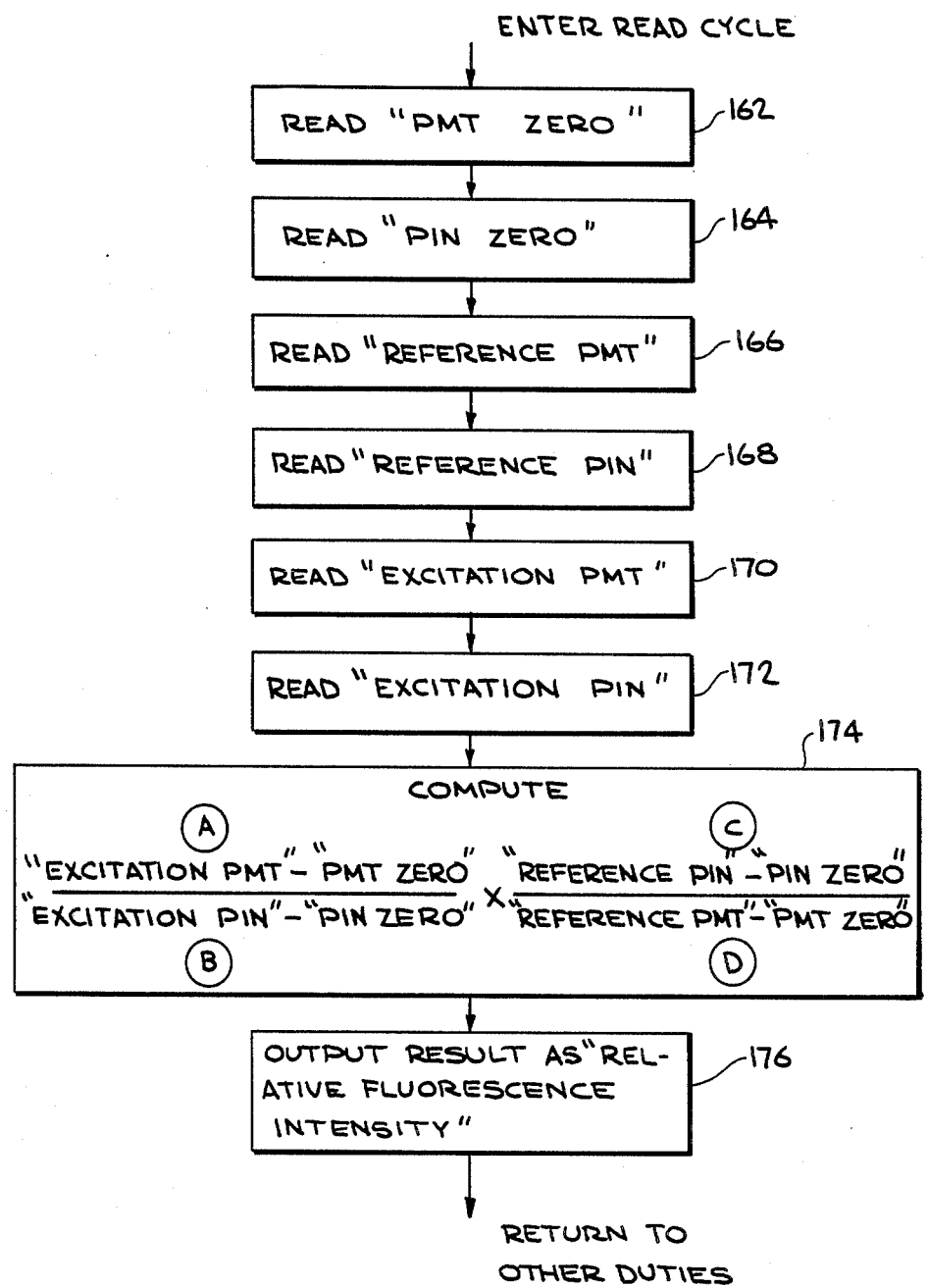
FIG. 6 is a flow diagram for the process of calculating the relative fluorescence intensity.
Figure 7:
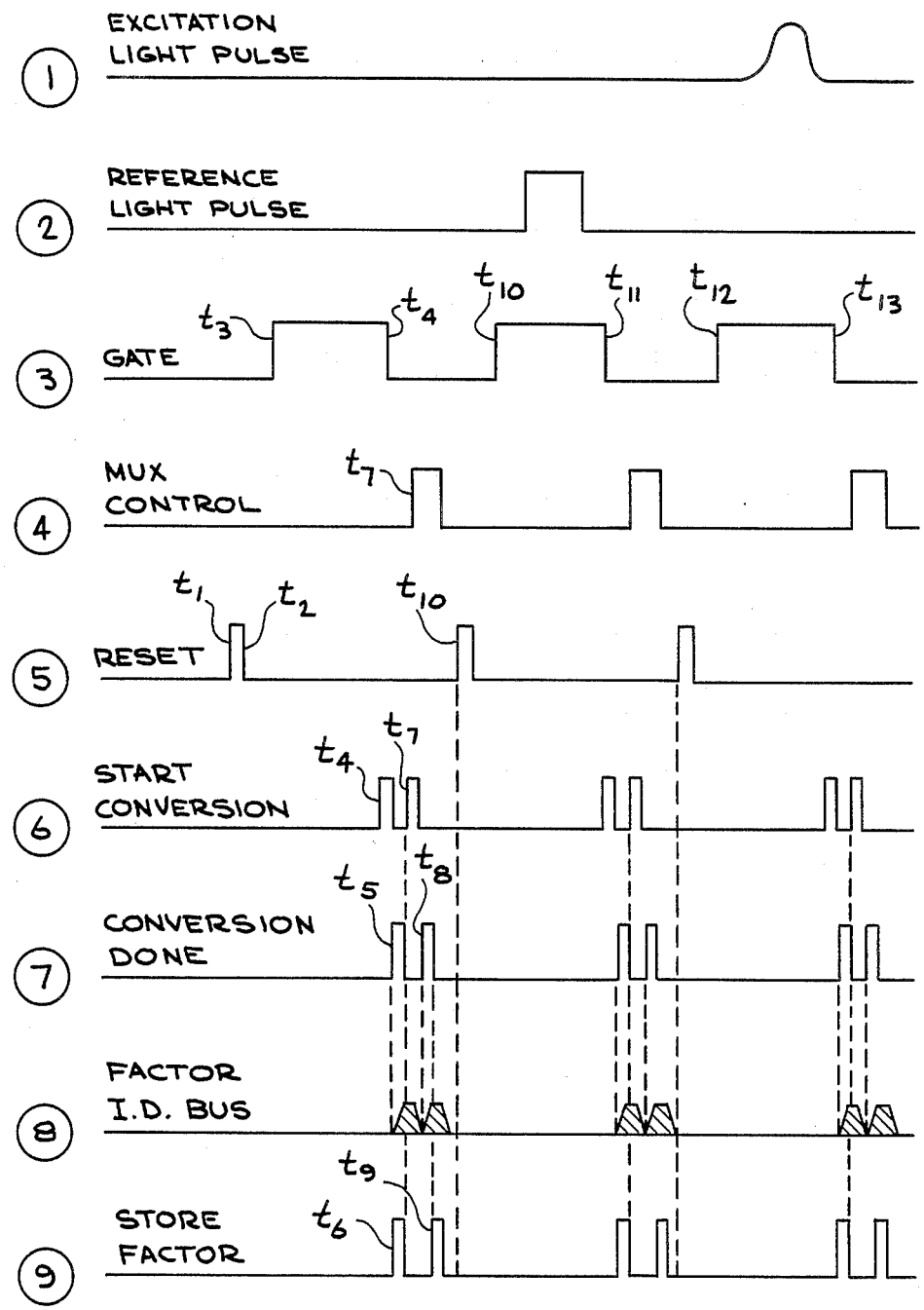
FIG. 7 is a timing diagram for the control signals used to control the electronic portion of the reference system to implement the process of FIG. 6.

Referring to FIGS. 6 and 7, the timing of the control signals to implement the calculation of the relative fluorescence intensity will be understood. FIG. 6 is a flow diagram of the steps the calculation circuit 134 and control logic 88 perform during a read cycle to evaluate a single excitation pulse and a single reference pulse. FIG. 7 is timing diagram illustrating the timing relationsips between the various control signals that are asserted during a single read cycle to implement the calculation of FIG. 6. The system is typically interrupt driven such that a high priority interrupt will be generated at some time before the excitation pulse is to be generated. This interrupt will vector processing to a routine which performs the steps of FIG. 6. In the preferred embodiment, the zero or base signal from each detector is read, i.e., the signal from each detector is read and stored in the absence of either an excitation pulse or a reference light pulse. The entry point of the routine of FIG. 6 is therefore a step 162 to read the "zero" light or baseline reference output from the photomultiplier tube 50.

Referring to FIGS. 5 and 7, the step 162 in FIG. 6 is implemented by asserting the RESET control signal on the line 110 between the times $t_1$ and $t_2$ on time line 5. This resets both of the gated integrators 106 and 118 thereby preparing them to integrate the signals coming from the photomultiplier tube 50 and the PIN diode 68. At time $t_3$ on time line 3, the GATE signal on line 108 is asserted which turns on both gated integrators simultaneously so that both start to integrate the "zero" light signals form the light detectors coupled to their respective channels. The GATE signal remains asserted until time $t_4$ at which time a START CONVERSION signal on a line 133, shown on time line 6 of FIG. 7, is asserted. This causes the A/D converter 130 to begin converting whatever analog signal is on the line 128 into a digital value. The signal which is on the line 128 is controlled by the state of the MUX CONTROL signal on the line 126, time line 4 in FIG. 7. At time $t_4$, MUX CONTROL is low thereby selecting the sample channel signal on the line 116 for connection to the line 128.

Note that there is no excitation or reference light pulse present between times $t_3$ and $t_4$ on time lines 1 and 2, so the conversion started at time $t_4$ by the START CONVERSION signal calculates the sample channel "zero" light value. After this sample channel zero value conversion is done, a CONVERSION DONE signal on a line 131, time line 7 in FIG. 7 is asserted at time $t_5$. This signal tells the control logic 88 that valid factor data is present on the factor bus 132. The control logic is programmed to know which factor is present on the bus 132, and this identification is sent to the calculation circuit 134 by setting the bits on a 3 bit FACTOR ID bus to identify which of the six factors or terms is currently valid on the bus 132. In some embodiments, the control logic 88 and the calculation circuit 134 are a single programmed microprocessor and the factor bus 132 is coupled to this single circuit. In such embodiments, there is no need for a FACTOR ID bus 135 since the identification of which factor is on the bus is already known to the microprocessor. The setting of the bits on the FACTOR ID bus is illustrated on time line 8 as starting at time $t_5$, but those skilled in the art will appreciate that this relative timing as well as the other relative timing relationships of FIG. 7 may have to be adjusted slightly to account for circuit delays. FIG. 7 illustrates the concepts of the invention only, and the timing of an actual system to implement the invention may deviate from FIG. 7 somewhat.

At a time $t_6$, a signal STORE FACTOR on line 137, illustrated on time line 9 of FIG. 7, will be asserted. Time $t_6$ is selected to be after time $t_5$ sufficiently that the data bits on the FACTOR ID bus are known to be valid. This STORE FACTOR pulse cause the calculation circuit 134 to read the data stored on the bus 132 and store it in the address identified on the FACTOR ID bus 135. In this manner, the "sample zero" term for the calculation to be performed by the routine illustrated in FIG. 6 calculated and stored and the step 162 in FIG. 6 is complete.

Next a step 164 is performed to calculate and store the zero or baseline value for the reference system light detector, PIN diode 68. The zero signal has already been integrated in the gated integrator 106 since this integration was started at time $t_3$ when the GATE signal was asserted. The gated integrator 106 holds the integrated value from the time $t_4$ much as a sample and hold circuit holds its sampled value after its sample signal goes inactive. At time $t_7$, the MUX CONTROL signal on line 126, time line 4, changes from low to high thereby selecting the output of the gated integrator 106 for coupling to the line 128. At approximately the same time or slightly later, the START CONVERSION signal on line 133 is reasserted and the conversion process starts. At some variable time $t_8$ later, the A/D converter 130 asserts the CONVERSION DONE signal which causes the control logic 88 to set the bits on the FACTOR ID bus 135 to identify the currently valid data on the bus 132 as the reference channel zero or baseline value. This setting of the bits on the bus 135 is symbolized on time line 8 starting at time $t_8$. After the bits on the bus 135 are valid at a time $t_9$, the control logic 88 asserts the STORE FACTOR signal on line 137 causing the calculation circuit 134 to read the data on the output bus 132 from the A/D converter 130 and store it in the address identified by the data on the FACTOR ID bus 135. That completes the step 164 in FIG. 6.

Next the routine of FIG. 6 causes the LED light source 70 in the reference system to be flashed. The steps to do this are not shown in FIG. 6, but their details will be apparent to those skilled in the art and the exact code to do this function is included in the Appendix attached hereto. The next two steps 166 and 168 in the routine of FIG. 6 are to read and store the electrical output signals from the photomultiplier tube 50 and from the PIN diode light detector 68, respectively, generated in response to the reference light pulse illustrated on time line 2 of FIG. 7. Note that the GATE pulse on time line 3 is asserted between times $t_{10}$ and $t_{11}$, times which overlap the time of occurrence of reference light pulse. The operation of the control logic 88 and the calculation circuit is the same and the timing of the control signals for reading the output signals from each light detector in response to the reference light pulse is the same as previously described with reference to the reading of the zero or baseline responses. The only differences are that a reference light pulse has occurred during the gating interval, and the addresses set on the FACTOR ID bus 135 on time line 8 are the addresses for the "reference PMT" and "reference PIN" terms.

The next two steps, 170 and 172, of the routine of FIG. 6 are to read and store the output signals of the photomultiplier tube and the PIN diode light detectors in response to the particular excitation light pulse that occurred during this particular read cycle. This excitation pulse is illustrated on time line 1 of FIG. 7. Again, the GATE signal on time line 3 is asserted between times $t_{12}$ and $t_{13}$, times selected to bracket the time of occurrence of the excitation light pulse. The operation of the control logic and the calculation circuit and the relative timing of the control signals to read and store the responses to this excitation pulse is the same as described above for the reading of the zero responses for the PMT and PIN light detectors except that the addresses written on the FACTOR ID bus 135 differ appropriately.

The final steps 174 and 176 in the routine of FIG. 6 are to make the calculation shown in step 174 and output the result as the "relative fluorescence intensity". The ratio calculated in step 174 is a complex ratio which is designed to cause the effects of variations in the baseline response of the detectors, or variations in the light intensity from one pulse to the next as well as other changes in the system other than changes in the target concentration of the sample, to cancel out leaving the "relative fluorescence intensity" stable for a stable target concentration. The ratio is comprised of two ratios multiplied together. These two ratios can be symbolically expressed as $(A/B) \times (C/D)$ where:

A = the amplitude of the response of the PMT to the fluorescent light emitted from the flow cell in response to the excitation light pulse that occurred during this read cycle less the PMT response in the absence of any light pulses;

B = the amplitude of the response of the PIN diode to the excitation pulse that occurred during this read cycle less the response of the PIN diode in the absence of any light pulses;

C = the amplitude of the response of the PIN diode to the reference light pulse from the LED that occurred during this read cycle less the response of the PIN diode in the absence of any light pulses; and D = the amplitude of the response of the PMT to the reference light pulse from the LED that occurred during this read cycle less the response of the PMT in the absence of any light pulses.

In operation of the system, the average relative fluorescence intensity from a large number of pulses, such as 100 excitation pulses and 100 reference pulses, is taken. This provides greater accuracy in the measurement. However, the arc lamp 20 excitation pulses can vary up to 5% in intensity from pulse to pulse. The intensity of the emitted fluorescent light is proportional to the intensity of the excitation light for a given concentration of targets. Thus, unless these variations in excitation light intensity are canceled out during the calculation of the relative fluorescence intensity, they will cause an apparent variation in the concentration of the targets despite the fact that the actual concentration did not change. It will be appreciated from the ratio calculated in step 174 of FIG. 6 that variations in the intensity of the excitation pulses from pulse to pulse will increase both the A and B terms equally. The resultant relative fluorescence intensity for each pulse will therefore remain the same regardless of the excitation pulse intensity. The need for a second light detector in the invention arises from the need to have the terms A and B to cancel out the effects of changes from pulse to pulse in the excitation pulse intensity. The second light detector need not be a PIN diode however since any light detector will suffice to perform the function of providing the B term.

There can also be drifts over time or temperature in the response characteristics of the PIN diode and the PMT light detectors for a given light intensity for the excitation light pulses. These changes will also cause an apparent change in the concentration of the targets where the reality is that the concentration has not changed. These changes in response can be canceled out if two readings from each detector are taken during each cycle and a ratio is calculated in which one of the readings from each detector is in the numerator and the other reading is in the denominator. Thus, if the response of one of the detectors changes from one cycle to the next for a given pulse intensity, both the numerator and denominator increase or decrease equally thereby canceling out the effect of the change. That is, if the PMT response drifts from cycle to cycle for equal light intensity in the excitation and reference light pulses, the terms A and D change equally, and the effect of the change is canceled. Likewise, if the response of the PIN diode changes from cycle to cycle, the terms C and B are equally affected, and the effect of the change on the relative fluorescence intensity is canceled. The need for these two light readings from each detector during each read cycle gives rise to the need for the second light source.

THE OPTICAL SYSTEM

Referring again to FIG. 6 there is shown a schematic diagram of the optical system of the invention. The function of the optical system is to conduct the two different sets of light pulses from the arc light 20 and the LED 70 to the two different detectors with a minimum of crosstalk and maximum stability.

The optical system is comprised of the arc light source 20 which generates pulses of excitation light. These pulses are directed into the collimating lens 28, and then are passed through the filter 30 the specifications for which have previously been given. The light pulses emerging from the filter 30 are passed through a focusing lens 36 which focuses the image of the wandering arc in the aperture 38 in the plane of the mask 40. The aperture 38 is approximately equal to the size of the input window for excitation light of the flow cell 22. The purpose of the aperture 38 in the mask 40 is to limit the geometric extents of the image of the moving arc to predefined boundaries. The reason for this is to minimize the amount of scattered excitation light scattered from the corners of the flow cell which gets into the optical channel carrying emitted fluorescent light toward the PMT 50. Scatter is minimized by sizing the aperture 38 such that when the image of the aperture is focused on the flow cell, no light energy falls on the edges of the flow cell outside the extents of the excitation light input window to be reflected or scattered toward the PMT.

The image of the aperture is then guided into the numerical aperture of a collimating lens 44 where the diverging light rays are captured and collimated into parallel paths. This beam of light is then projected through the beam splitter 46 to a focusing lens 48. The lens 48 focuses the image of the aperture 38 on the excitation light input window of the flow cell 22.

Figure 9:
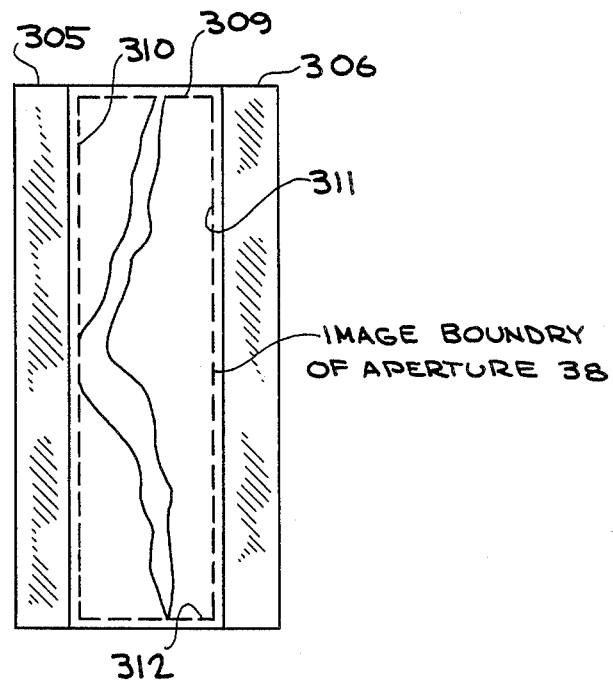
FIG. 9 is a side view of the flow cell used in the fluorometer of the invention.
Figure 10:
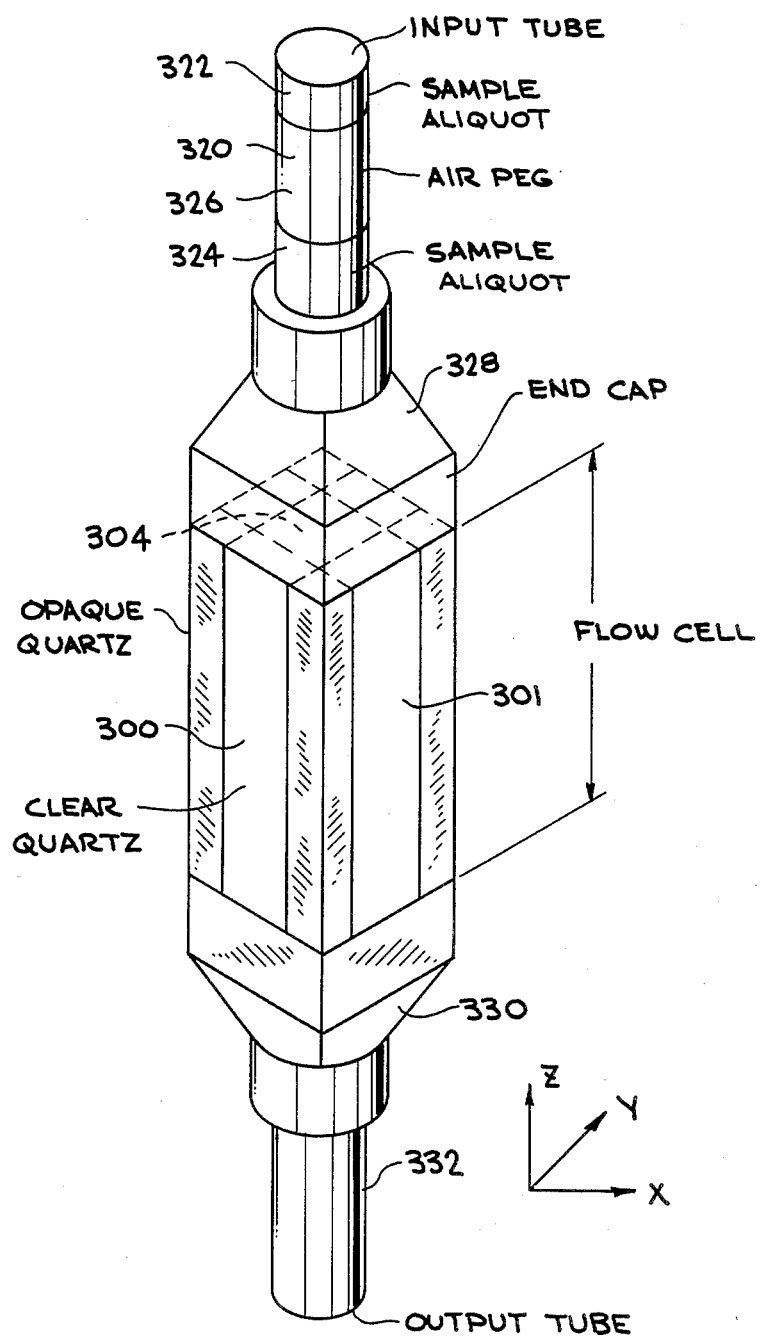
FIG. 10 is a perspective view of the flow cell used in the invention along with the end caps.

FIG. 10 shows a top view of the flow cell, and FIG. 9 shows a front view of the flow cell excitation light window. The flow cell is constructed of four windows 300 through 303 of clear quartz glass arranged into an array defining a rectangular cavity 304 in which the fluid suspension of the tagged targets resides. The corners 305 through 308 of the flow cell are constructed of opaque black quartz. These corner pieces have the same thickness as the clear quartz windows, and they are bonded to the clear quartz windows at the corners so as to form an opaque extension of each clear quartz window panel thereby defining the boundaries of transparency of each window. The clear quartz window panel 300 flanked by the opaque quartz corner pieces 305 and 306 defines the transparent boundaries of the excitation light window. This excitation light window is shown in FIG. 9 which is a view taken from the view line 9—9' in FIG. 10. FIG. 9 shows the desired placement of the image of the aperture 38 through the excitation light window and inside the flow cell cavity 304.

It is desirable to adjust the placement of the lens 48 and select the shape of the lens 48 such that the focal point on the image side is inside the flow cell cavity 304. It is also desirable to adjust the placement of the mask 40 relative to the focal point of the lens 48 on the object side and to select the size of the aperture 38 relative to the size of the excitation light window such that the entire image of the aperture 38 can be contained in the cavity 304 of the flow cell. All rays making up the image of the aperture 38 should pass through the excitation window 300 without touching the opaque corners 305 or 306. If some rays strike the corners, there will be some reflectance since the air and quartz indices of refraction do not match. Such reflectance will occur anyway at the boundaries between the quartz and the air and the quartz and the liquid inside the flow cell. Such reflectance is undesirable, because it contributes to noise in the system in the form of increased scattered light from the excitation channel into the emitted light channel. It would be desirable to exactly match the index of refraction of the flow cell walls to the index of refraction of the air and to match the index of refraction of the fluid inside the flow cell to the index of refraction of the walls of the flow cell. However, this is not currently possible in a practical embodiment.

There will exist scattered light from dust particles and particles in the solution and there will exist reflected light from the various structures and boundaries between materials of different indexes of refraction. Because of this unavoidable fact, some light rays will have proper angles of incidence to be captured inside the quartz walls of the flow cell by internal reflection. That is, some of the rays will intersect the interface between the quartz and the outside medium of a lesser index of refraction at greater than the critical angle. Such a ray will be reflected back into the quartz as the ray 316 shown in FIG. 10. The purpose of the opaque corners 305 through 308 is to prevent the escape of most of these captured rays into the emitted light channel where they could be detected as noise.

An exemplary image of a typical arc during a pulse is shown in FIG. 9. Note that this particular arc has wandered outside the boundary of the aperture, and has been clipped by boundary of the aperture 38 in the mask 40 of FIG. 6 so that no light from the arc image falls on the end pieces 305 and 306 of the flow cell. The boundaries of rays forming the image of the aperture 38 in the flow cell as they pass through the excitation light window are illustrated by the dashed lines 309 through 312. Typically the arcs of each excitation light pulse also create a glowing region of gas surrounding the arc. The light from this glowing region of gas is also clipped by the aperture 38 in the mask 40 so that the light in the image of this glowing region does not fall on the opaque corners of the flow cell excitation light window where it might be scattered into the emitted light optical light channel.

Any excitation light that passes through the flow cell is reflected back into the flow cell by the mirror 23, and excites more dye molecules on the second pass through the target region. Emitted light from excited fluorophore molecules which is emitted in the direction of the clear quartz window 303 is reflected by the mirror 25. It then passes out through the emitted light window 301 along with photons emitted in the direction of the window 301. This emitted light is in the form of a nebulous glowing area in the fluid inside the cavity 304, the image of the arc projected inside the cavity 304 having been destroyed or spatially integrated by the spherical emission of the emitted photons in the cavity 304.

This emitted fluorescent light is emitted at various angles some of which are diverging. The emitted light is reflected by a mirror into a lens 52 which collimates the light into a beam which is passed through the bandpass filter 54. The characteristics of this filter have been previously defined. Its purpose is to filter out any scattered or refracted excitation light which has found its way into the emitted light optical channel.

The filtered light beam emerging from the filter 54 is passed through a focusing lens 56 which brings the image of the emitted light output window 301 of the flow cell to a focus in the aperture 58 of the second mask 60. The size of the aperture 58 and its placement relative to the face of the cathode in the PMT is such that the diverging rays from the image of the emitted light output window window in the aperture 58 cover substantially all the face of the cathode of the PMT without exceeding its boundaries.

The second light source in the system is the green light emitting diode 70. This light emitting diode has its own lens, and emits a directional, positionally stable beam of light which is aimed generally at the PIN diode light detector 68 through a beam splitter 72. Most of the light from the LED 70 passes through the beam splitter and falls upon the face of the PIN diode where it is converted into an electrical signal. The beam splitter 72 deflects a portion of each reference light pulse emitted from the LED 70 through the filter 74. The filter 74 is designed to pass the green reference light pulses, but to block any blue excitation light from getting through to the PMT. The reference light pulses emerging from the filter 74 enter a mirrored wall cavity 76 with walls which causes internal reflection of the image of the LED 70 between the walls. This spatially integrates the image of the LED thereby destroying the LED image although this is not necessary since the image of the LED is stable and does not wander such that it needs to be spatially integrated. The reference light pulses then emerge from the cavity and fall upon the photocathode of the PMT.

The other portion of the reference system is the light pipe 64 and its associated lens. Because it is necessary to conduct a portion of each excitation light pulse to the PIN diode 68 for detection, the beam splitter 46 is used. The beam splitter deflect a portion of each excitation pulse into the lens 62. The lens 62 focuses the image of the aperture 38 onto the face of a clear plastic light pipe 64. The light pipe guides the light captured in the pipe to the lens 66 through many internal reflections. In the process, the image of the aperture 38 is destroyed such that the end of the light pipe closest to the lens 66 looks like a glowing disk with no image visible.

The light of the excitation pulses emerges from the light pipe 64 at many different angles. This light must be focused or at least converged onto the face of the PIN diode 68. This is done by the lens 66 which captures as much of the emerging light as possible. This light is then focused upon the face of the PIN diode such that substantially all of the light emerging from the light pipe is projected upon the face of the PIN diode.

THE FLOW CELL

Figure 8:
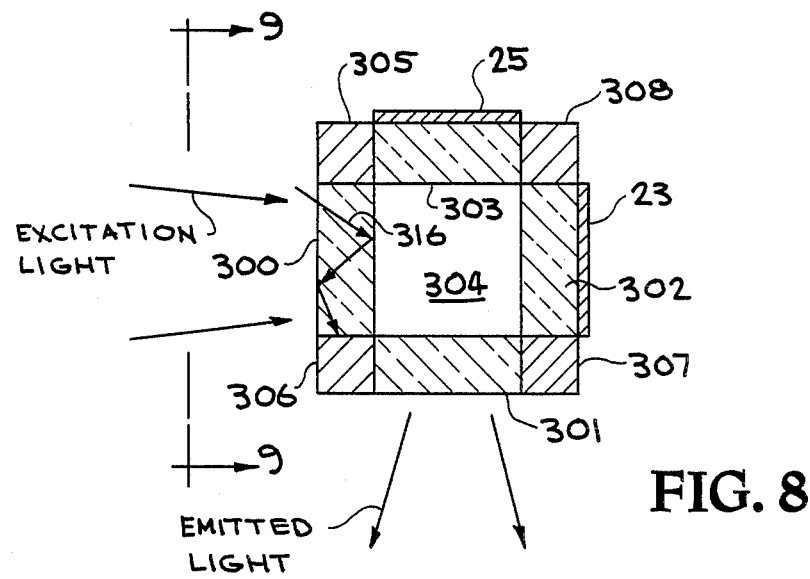
FIG. 8 is a top view of the flow cell used in the fluorometer of the invention.

The flow cell is selected to have the long narrow geometry of FIGS. 8 and 9 to provide a better shape for cleansing of the flow cell by "air pegs". A typical flow cell arrangement is shown in FIG. 10. An input tube 320 carries sample aliquots 322 and 324 separated by an air peg 326. These aliquots and air pegs are moved through the end cap 328 into the flow cell one sample aliquot at a time. That is, one sample aliquot will be moved into the flow cell and assayed, and then the air peg between that sample and the next sample will be moved through the flow cell. The purpose of the air peg is to sweep the walls clean of the remnants of the sample preceding it before entry into the flow cell of the sample following the air peg. The purpose of the end cap is to aid in a smooth fluid dynamic transition between the round shape of the input tube 300 and the square or rectangular shape of the internal cavity 304 of the flow cell. A similar end cap 330 on the opposite end of the flow cell aids in the transition from the square shape of the flow cell cavity 304 to the round shape of the output tube 332.

The flow cell in FIG. 10 has the construction of FIGS. 8 and 9. The input window 300 for receiving excitation light pulses is shown at the front of the structure in FIG. 10. The mirrored surface 23 for reflecting the excitation energy back into the internal cavity 304 is on the opposite side from the input window 300 along the y axis. The output window 301 is shown at the right side in FIG. 10. The mirrored surface 25 which reflects emitted fluorescent light back into the flow cell is on the left or opposite side from the window 301 along the x axis. Any orientation of these two windows will suffice, but it is desirable to have the two window on orthogonal faces of the flow cell to minimize scatter of the excitation light into the optical channel that guides the emitted fluorescent light. The mirrored surfaces 23 and 25 may be on either the inside surface or the outside surface of the flow cell walls, but they are preferably on the outside walls.

What is claimed is:
1. An apparatus comprising:

an arc light means having electrodes, for exciting a variable unknown and very small quantity of fluoroescent dye chemically attached to a material being assayed with intense excitation pulses of light generated from an arc occurring between said electrodes, said excitation light pulses having at least some wavelengths in the excitation band of said fluorescent dye;

flow cell means for containing said material to which said fluorescent dye molecules are attached, said flow cell having a flat, transparent input window of quartz glass having a shape which is longer in one dimension than the other, said longer dimension having an axis which is parallel to the axis between said electrodes in said arc light means between which said arc appears, said flow cell also having a flat, transparent exit window of quartz glass having a normal which is at right angles to the normal of said input window, said exit window being the path through which fluorescent light emitted by excited dye molecules travels, said flow cell having at least the intersection of said input window and said exit window formed by opaque material so as to block the path of scattered light traveling inside the input window toward said exit window by refraction between the quartz surfaces thereby preventing such scattered light from entering the paths used by light exiting from said exit window;

first mask means in the optical path between said arc light means and said input window for limiting the image of the arc from wandering on the surface of said flow cell outside the bounds of said input window;

photomultiplier tube means for detecting fluorescent light emitted from said dye in response to said excitation light pulses and for generating signals indicting the intensity of said light emitted from said dye;

means for focusing emitted fluorescent light on said photomultiplier tube means and for allowing only light rays emanating from the interior of said flow cell means and having a frequency in the band of fluorescent light frequencies emanating from excited dye molecules to reach said photomultiplier means and for preventing stray excitation light scattered from the walls of said flow cell means from following the path traveled by said fluoroescent light rays emanating from the inside of said flow cell means;

reference light detector means for detecting the intensity of light pulses shining on a light sensitive surface and for generating an output signal indicating said intensity;

light waveguide means for coupling light from said arc to said reference light detector means and for spatially integrating the image of said arc so that there is no arc image that wanders randomly over said light sensitive surface of said reference light detector means;

reference light source means for supplying pulses of reference light to each of said photomultiplier tube means and to said reference light detector means during the dark intervals between excitation light pulses; and means for calculating a relative fluorescence index from the output signals from said reference light detector means in response to both said excitation light pulses and said reference light pulses and from the output signals from said photomultiplier tube means in response to both emitted fluorescent light pulses and reference light pulses, said relative fluorescence index indicating the amount of fluorescent light being emitted from said flow cell and being compensated for changes in intensity of either the reference light pulses or the excitation light pulses and being compensated for changes in the sensitivity of either said photomultiplier tube means or said reference light detector means.

2. Apparatus as defined in claim 1 wherein said flow cell means includes a mirrored surface opposite said input window to reflect excitation light pulses back through said dye and a mirrored surface opposite said exit window for reflecting emitted fluorescent light rays traveling away from said exit window toward said exit window.

3. Apparatus as defined in claim 1 wherein said flow cell means includes means for containing said dye in a confined space with a geometry which is longer in one dimension than the other.

4. Apparatus as defined in claim 3 further comprising means for spatially integrating the image of said arc on said dye.

5. The apparatus of claim 1 wherein said means for calculating comprises:
means for calculating the ratio
$(A/B) \times (C/D)$ where A = the magnitude of the output signal from said photomultiplier tube means generated in response to receipt of fluorescent light from said dye emitted in response to excitation of said dye by an excitation light pulse, and B = the magnitude of the output signal from said reference light detector means in response to receipt of a portion of the same excitation light pulse which caused response A after being spatially integrated by said light waveguide means, and C = the magnitude of the output signal from said reference light detector means in response to receipt of a reference light pulse from said reference light source means, and D = the magnitude of the output signal from said photomultiplier tube means generated in response to receipt of the same reference light pulse from said reference light source means that caused response C.

6. The apparatus of claim 5 wherein the terms A, B, C and D are as defined less the magnitude of the response of the respective detecting means when not receiving a light pulse.

7. The apparatus as defined in claim 5 wherein said eight waveguide means is a light pipe.

8. The apparatus of claim 1 wherein said flow cell means has a geometry which is selected to conform to the general shape of the volume through which said arc wanders.

9. A reference system for a fluorescence measuring system having a flow cell containing fluorescent dye having an excitation band of frequencies and an emission band of frequencies, a first light source having an arc between two electrodes for illuminating said dye in said excitation spectrum, and a first light detector for detecting fluorescent light in said emission spectrum emitted from said dye comprising:
means for causing said first light source to emit multiple pulses of light separated by dark intervals;

means for reducing the amount of light in said excitation spectrum light pulses from said first light source which is scattered to said first light detector and for maximizing the amount of fluorescent light emitted in said emission spectrum which reaches said first light detector comprising transparent excitation and exit light windows in said flow cell which have faces which are at right angles to each other, said flow cell comprising a chamber having a rectangular shaped cross-section and having opaque corners to cut off the path of light rays traveling in said excitation light window toward said exit light window, said excitation light window having a long dimension and a short dimension of a transparent portion, said long dimension parallel to the line between said electrodes, and further comprising a lens, a mask means and filter means between said arc and said excitation light window, said mask means for limiting an image of said arc created by said lens from wandering outside said transparent portion, said filter means for reducing the amplitude of any light from said arc in the emission spectrum which reaches said flow cell;

a second light detector;
means for diverting a portion of each said pulse from said first light source to said second light detector;
a second light source;
means for causing said second light source to emit multiple pulses of light during the dark intervals of said first light source;
means for directing a portion of each said pulse of light from said second light source to each of said first and second light detectors;
means for quantifying the signals from said first and second light detectors in response to said light pulses from said first and second light sources; and
means for calculating the ratio $RFI = (A/B) \times (C/D)$ where A = the response of said first light detector to fluorescent light emitted from the dye in said flow cell emitted in response to a pulse from said first light source less the response of said first light detector in the absence of any said pulse or other light;

B = the response of said second light detector to a portion of the same said light pulse from said first light source which caused response A less the response of said second light detector in the absence of any said pulse or other light;

C = the response of said second light detector in response to a light pulse from said second light source less its response in the absence of said pulse or any other said light; and D = the response of said first light detector in response to the same light pulse from said second light source that caused response C less its response in the absence of said pulse or any other light, and RFI = the relative fluorescence index of said dye.

10. An apparatus comprising:
a flow cell containing a material being assayed, said material being tagged with a fluorescent dye and having a transparent input window for allowing excitation light to impinge on said dye and a transparent output window for allowing fluorescent light emitted in response to said excitation light to exit;

an excitation arc light source for generating excitation light pulses from an arc having a frequency in the excitation spectrum of said dye;

a first optical path means for guiding said excitation light pulses and focusing the image of said arc onto the dye inside said flow cell through said transparent input window, and for filtering out any light not in the excitation spectrum of said dye from entering said flow cell;

means in said first optical path for limiting the light energy in the image of said arc to an area within a predetermined area on the face of said flow cell having a geometry generally conforming to the geometry of said transparent input window;

means for spatially integrating the image of said arc in said dye;

a photomultiplier tube light detector having a light input;

a second optical path for guiding emitted fluorescent light emerging from said transparent output window to the light input of said photomultiplier tube and for focusing the emitted fluorescent light onto the light sensitive surface of said photomultiplier tube and for filtering any light not in the frequency band of said emitted fluorescent light and for limiting the shape and size of the image of said flow cell projected onto the light sensitive surface of said photomultiplier tube;

a beam splitter in said first optical path for diverting a portion of each said excitation light pulse to an output;

a light pipe having an optical input optically coupled to said output of said beam splitter and having an optical output;

a second light detector having a light sensitive surface located such that light emerging from the output of said light pipe falls upon said optical input of second light detector;

a lens interposed between said light output of said light pipe and the light sensitive surface of said second light detector for capturing light emerging from said light output and focusing it upon said light sensitive surface of said second light detector;

a reference light source of generating reference light pulses which occur during dark intervals between excitation light pulses; and a third optical path for guiding a portion of each reference light pulse to said light sensitive surface of said second light detector and a portion of each reference light pulse to the light sensitive surface of said photomultiplier tube.

11. The apparatus of claim 10 further comprising means coupled to said photomultiplier tube and to said second light detector for calculating the relative intensity of fluorescent light emitted from said flow cell in a manner which yields a result which is substantially independent of all changes in the system except changes in the amount of dye molecules in said flow cell.

12. The apparatus of claim 11 wherein said means for quantifying includes means for calculating a first ratio equal to the response of said photomultiplier tube to each excitation light pulse divided by the response of said second light detector to each excitation light pulse and for multiplying said first ratio by a second ratio equal to the response of said second light detector to each reference light pulse divided by the response of said photomultiplier tube to each said reference light pulse.

13. The apparatus of claim 12 further comprising means for subtracting from each response of each term in the numerator and the denominator of each said ratio, the response of the respective detector in the absence of any light pulse.

14. A process for quantifying the amount of fluorescent dye in a flow cell comprising the steps of:

exciting the dye with an excitation light pulse from an arc which wanders in space between two electrodes, said light from said arc having been focused, and passband filtered so that only excitation light frequencies impinge on the dye and said arc light having been passed through a mask of predetermined geometry such that said arc light is masked such that the wandering of the image of the arc on the dye is limited to within a known geometric area;

guiding the resulting emitted fluorescent light to a first light detector with a lens, and a passband filter and a mask to focus the emitted fluorescent light in a beam, filter out light rays having a frequency other than the frequency of the emitted fluorescent light and to limit the geometry of the image of the flow cell on the light sensitive surface of the first light detector;

calculating the amount of fluorescent light emitted from said dye in response to said excitation light pulse using said first light detector and storing it as a variable A;

guiding a portion of said excitation pulse to a second light detector and spatially integrating the image of the excitation light source in the process;

calculating the amount of light from said excitation light pulse falling upon said second light detector and storing it as a variable B;

generating a reference light pulse;

guiding a portion of said reference light pulse to each of said first and second light detectors;

calculating the amount of said reference light pulse falling on said second light detector and storing it as a variable C;

calculating the amount of said reference light pulse falling on said first light detector and storing it as a variable D; and calculating the ratio $$A/B$$

and multiplying it by the ratio $$C/D.$$

15. The method of claim 14 further comprising the steps of calculating the amount of light falling on said first light detector in the absence of any light pulse and storing it as the variable Z1 and calculating the amount of light falling on said second light detector in the absence of any light pulse and storing it as the variable Z2 and wherein the last step in the method of claim 24 is modified to calculate $$(a-z1/b-z2) \times (c-z2/d-z1)$$

16. The method of claim 15 further comprising the step of blocking the transmission of substantially all of said excitation pulse to said first detector so that the variable A indicates substantially only the amount of fluorescent light emitted from said dye in response to said excitation pulse.

17. An apparatus as defined in claim 9 wherein said flow cell includes a mirrored surface opposite said excitation light window to reflect excitation light pulses back through said dye and a mirrored surface opposite said exit light window for reflecting emitted fluorescent light rays traveling away from said exit light window toward said exit light window.

18. An apparatus as defined in claim 14 further comprising means in the light path between said flow cell and said first light detector for filtering out any light not having a frequency in the frequency band of fluorescent light emitted by said dye and for focusing emitted fluorescent light on said first light detector and for limiting the extent of the image of said exit light window on the light sensitive surface of said first detector.

* * * * *